Figure 1:
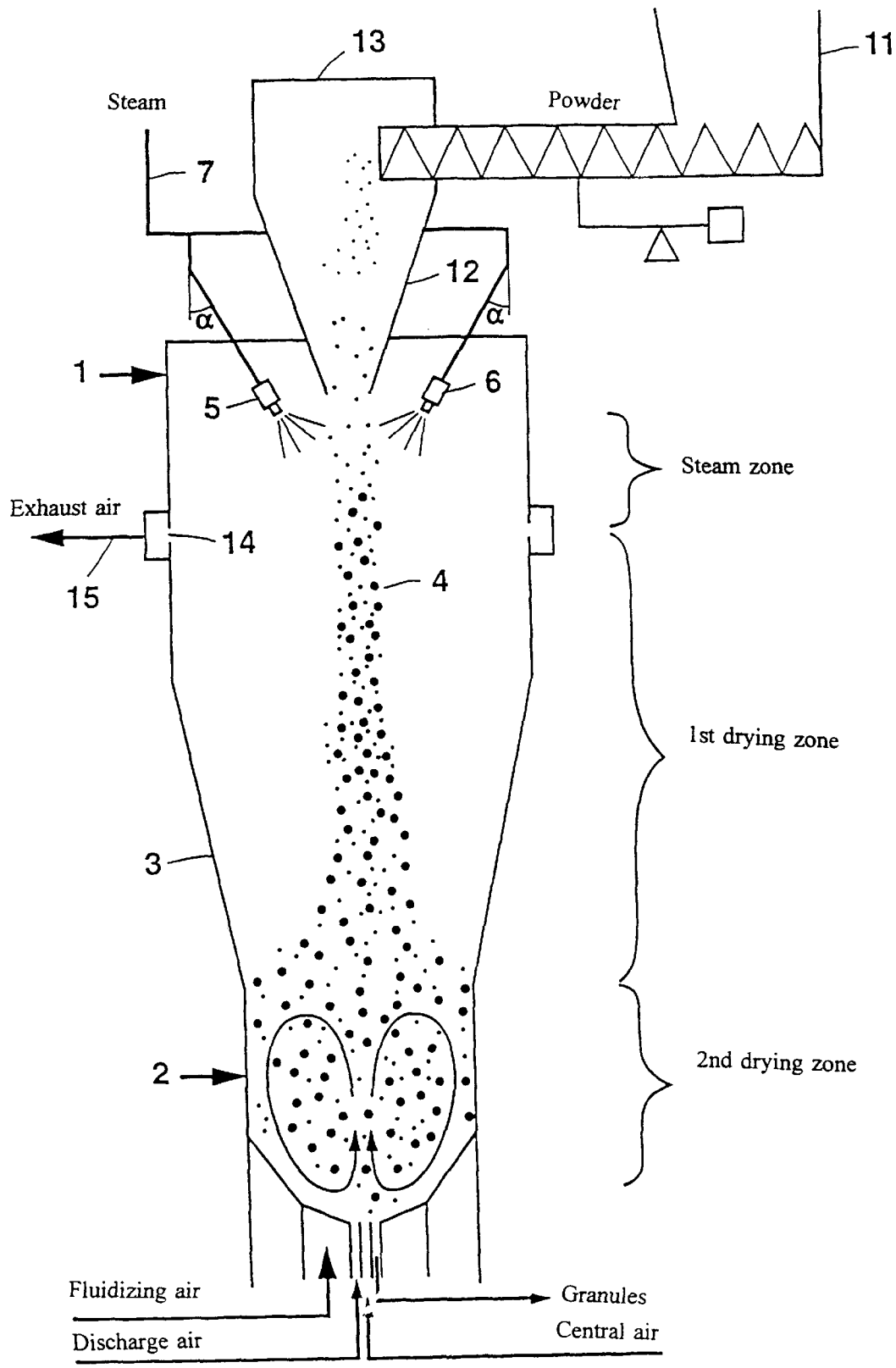

United States Patent [19]
Seyffert et al.

[11] Patent Number: 5,955,036
[45] Date of Patent: Sep. 21, 1999

[54] PROCESS AND APPARATUS FOR THE AGGLOMERATION OF HYDROLYTICALLY SENSITIVE SUBSTANCES BY MEANS OF STEAM

[75] Inventors: Ina Seyffert, Köln; Hans Uhlemann, Solingen; Reinhardt Walter, Leverkusen, all of Germany; Joachim Martin Maasz, Station, N.J.

[73] Assignee: Bayer Aktiengesellschaft, Leverkusen, Germany

[21] Appl. No.: 09/240,033

[22] Filed: Jan. 29, 1999

Related U.S. Application Data

[62] Division of application No. 08/832,894, Apr. 3, 1997.

[30] Foreign Application Priority Data

Apr. 9, 1996 [DE] Germany .......................... 196 14 063
Jun. 12, 1996 [DE] Germany .......................... 196 23 410

[51] Int. Cl.⁶ .................... C08F 5/02; B05D 7/00
[52] U.S. Cl. .................... 422/139; 422/145; 427/213; 208/426; 514/165; 424/489
[58] Field of Search .................... 422/139, 145; 427/213; 208/426; 514/165; 424/489

[56] References Cited

U.S. PATENT DOCUMENTS

| | | | |
|---|---|---|---|
| 3,143,428 | 8/1964 | Reimers et al. | 99/141 |
| 4,556,175 | 12/1985 | Motoyama et al. | 241/57 |
| 4,946,654 | 8/1990 | Uhlemann et al. | 422/140 |
| 5,082,634 | 1/1992 | Raufast | 422/143 |
| 5,536,430 | 7/1996 | Fues et al. | 510/535 |

FOREIGN PATENT DOCUMENTS

| | | |
|---|---|---|
| 0163836A1 | 12/1985 | European Pat. Off. . |
| 0202076 | 11/1986 | European Pat. Off. . |
| 0787437A2 | 8/1997 | European Pat. Off. . |
| 1940915 | 2/1971 | Germany . |
| 2125155 | 11/1972 | Germany . |
| 1792752 | 2/1975 | Germany . |
| 4234376A1 | 4/1994 | Germany . |
| 4340015 | 6/1995 | Germany . |

*Primary Examiner*—Cecilia J. Tsang
*Assistant Examiner*—Fabian A. Jameison
*Attorney, Agent, or Firm*—Sprung Kramer Schaefer & Briscoe

[57] ABSTRACT

In the process for the agglomeration of slightly soluble and hydrolytically sensitive substances, a powder of the slightly soluble substance is conducted, together with at least one water-soluble binder, in free fall through a steam atmosphere at temperatures between 85° C. and 105° C. essentially without the action of compacting forces. In this process, the residence time in the steam atmosphere is approximately 0.5 to 10 seconds. The agglomerates formed are then dried in free fall, so that small solid bridges form from the binder liquid bridges formed at the points of contact between the primary particles. In a following integrated fluidized-bed dryer, the final drying then takes place to a water content of less than 0.5% by weight. The process is carried out in a steam jet agglomerator in which a freely falling product curtain of the pulverulent mixture to be agglomerated is impinged by steam using steam jet nozzles (5, 6). A fluidized-bed dryer (2) is connected at the lower part of the agglomerator (1) in such a manner that the agglomerated particles (4) fall directly into the fluidized bed.

6 Claims, 4 Drawing Sheets

PROCESS AND APPARATUS FOR THE AGGLOMERATION OF HYDROLYTICALLY SENSITIVE SUBSTANCES BY MEANS OF STEAM

This application is a divisional of Ser. No. 08/832,894 filed Apr. 3, 1997.

The invention relates to a special process for the agglomeration of slightly soluble and hydrolytically sensitive substances, in particular pharmaceutical active substances, such as acetylsalicylic acid (ASA), by using steam. In addition, the invention relates to an apparatus for carrying out the process.

Many substances in powder form are difficult to disperse in liquids, and therefore their use for dispersions or solutions is often troublesome. Frequently, moreover, good flow behaviour and a very low dust content are desired. This also applies to slightly soluble powders which can have both hydrophilic and hydrophobic surface properties. If powders are used for pharmaceutical preparations, it is, furthermore, frequently desirable or necessary to improve or mask tastes or to avoid or minimise contact with other incompatible mixing components.

The improvement in the wetting, flowability and the reduction of the dust content in the use of powders is customarily achieved by granulating the relevant powders by a process of agglomeration. Agglomeration processes are characterized by the use of granulating liquids, customarily water or aqueous solutions. These processes are therefore not applicable to processing hydrolytically sensitive substances, since in this case, generally, the (active) substance decomposes, with the formation of (pharmaceutically) undesirable degradation products. If, therefore, non-aqueous organic solvents are used, this leads to solvent residues in the granules which are likewise undesirable or impermissible. Furthermore, working with a solvent increases the expenditure on processing.

It has been found that readily dispersible granules are obtained if the agglomeration process produces, between the primary particles, very small solid bridges which can be easily broken up on redispersion in a liquid and preferably comprise a material which is freely soluble in the liquid. It is further advantageous here for the ready dispersibility of the granules if, during the agglomeration, i.e. in the still moist state of the granules, compacting forces are avoided, since otherwise the points of contact between the moistened particles are enlarged and relatively large relatively stable solid bridges are formed.

The invention relates to a process for the agglomeration of hydrolytically sensitive substances, in particular ASA, characterized in that the slightly soluble ASA powder is conducted together with at least one freely water-soluble pulverulent binder in free fall through a steam atmosphere at temperatures between 85° C. and 105° C., preferably at approximately 100° C., essentially without the use of compacting forces, with a residence time in the steam zone of approximately 0.5 to 10 seconds, preferably 1 to 3 seconds, and is then initially dried in further free fall so that, at the points of contact between the particles of the water-insoluble active substance and the water-soluble binder, small solid bridges are formed from the liquid bridges which are formed owing to the condensation and in which binder is dissolved, and in a subsequent drying operation in an integrated fluidized bed is dried to a water content of less than 5% by weight, preferably less than 1% by weight.

"Small solid bridges" is taken to mean that the solid bridges should have a mean transverse dimension (diameter or thickness) of 1 $\mu$m to 30 $\mu$m, preferably 5 to 15 $\mu$m.

As a result of the fact that the contact time of the water with the hydrolytically sensitive powder is very short, and also the heat stress of the solid particles at a maximum of 100° C., preferably at a maximum of 86° C., is low and is present only very briefly, no significant degradation reactions occur during the process according to the invention.

The partial solution of the particle surface of the binder by the condensed steam proceeds very rapidly, the resulting solutions form liquid bridges at the contact points between the particles or are drawn on to the slightly soluble hydrolytically sensitive particles. The immediate evaporation of the water occurring after the agglomeration with the formation of solid bridges (or partial) encasing of the insoluble active substance particles by the water-soluble auxiliaries ensures stability even in the case of hydrolytically sensitive substances, such as ASA.

Using the method described, if suitable ratios of active substance and auxiliary and expedient process conditions are selected, a type of microencapsulation or coating of the water-insoluble substances is also possible.

For the agglomeration or (partial) microencapsulation of the slightly soluble or insoluble substances, freely water-soluble binding auxiliaries are used, such as polyvinylpyrrolidone (PVP), PVP derivatives, starch, starch and cellulose derivatives, sugars, sugar alcohols such as sorbitol, xylitol, sugar derivatives such as maltodextrin, isomaltose, fruit acids and their water-soluble salts, such as citrates or tartrates, ascorbic acid, amino acids or inorganic salts such as sodium sulphate.

The weight ratio of the slightly soluble active substances to the water-soluble binding auxiliaries is 1 to 10 to 10 to 1, preferably 3 to 8 to 7 to 2. The mixture to be agglomerated of hydrolytically sensitive insoluble active substance and water-soluble auxiliary is advantageously introduced into the apparatus from the top, together with the steam in spatial proximity. The steam condenses on the colder powder particles, the condensate film partially dissolves the binder, and the liquid bridges formed at the contact points between the moistened particles are dried to form solid bridges. In the case of a great excess of water-soluble auxiliaries, the hydrolytically sensitive active substance can be completely shielded by the water-soluble auxiliary. The process can also be employed in such a manner that a freely water-soluble active substance acts as binder.

An essential element of the process according to the invention is the use of a virtually pure steam atmosphere for the direct moistening of the particle surface. If air were simultaneously present, air cushions to the particle surface would otherwise have to be crossed by the steam by diffusion. As a result, less steam can condense on the solid, and there is thus a lower degree of agglomeration or shielding of the active substance. Thus, the aim of treating the hydrolytically sensitive powder cannot be achieved, or is achieved to only an unsatisfactory extent.

To carry out the process according to the invention, an apparatus has proved useful which comprises an agglomerator having a closed housing, at the upper end of which a metering apparatus for a pulverulent material connected to a feed hopper is mounted by which a freely falling product curtain of pulverulent material in the agglomerator is produced. In addition, the apparatus is equipped in the upper part of the agglomerator with nozzles for producing steam jets which at least partially surround the freely falling product curtain within a steam zone. The characteristic according to the invention of this apparatus is that at the lower part of the agglomerator, a fluidized-bed dryer is connected in such a manner that the agglomerated particles fall directly into the fluidized bed. The fluidized-bed dryer is thus directly integrated into the steam jet agglomeration apparatus.

Advantageously, the steam jet nozzles consist of tubes or bore holes which are connected to a distributor tube extending in the longitudinal direction of the agglomerator, one distributor tube being arranged at each of the two sides of the product curtain.

An essential element of the apparatus according to the invention is also the separation of the steam zone (moistening zone) from the drying zone. This separation is achieved according to a further development of the invention by means of the fact that a heated double-walled protective tube which encloses the steam jet nozzles in the upper part of the agglomerator is arranged and through the jacket of which protective tube exhaust air is taken off. In this manner, all of the gas streams introduced into the apparatus by the fluidized-bed dryer can be taken off at the lower end of this protective tube.

Alternatively, the steam zone can also be separated from the drying zone by means of the fact that a ring gap having a collection channel to take off the exhaust air is provided on the agglomerator housing at a distance of 50 mm to 300 mm from the lower end of the steam jet nozzle distributor tubes. In this manner, likewise, all of the exhaust air can be taken off evenly over the entire periphery of the apparatus in the region between the evaporation and drying sections.

A preferred development of the apparatus according to the invention is that the fluidized-bed dryer integrated into the steam jet agglomerator has an annular conically ascending outer fluidizing plate and a central inner fluidizing plate, the flow velocity of the fluidizing air exiting at the inner plate being greater than the flow velocity of the fluidizing air at the outer plate.

Advantageously, connected to the conical outer fluidizing plate is a likewise conical widening of the agglomerator housing. These measures cause a circulating motion of the bed and prevent an undesirable local overmoistening. The desired final moisture can be set by an appropriate residence time in the drying zone and/or appropriate choice of the drying air rate and drying air temperature in the fluidized bed. The temperature in the fluidized bed in this case is between 20° C. and 70° C.

By means of the invention, the following advantages are achieved:

On account of the low agglomeration moistures, temperature stress and, especially, the very short stress duration, even hydrolytically sensitive products may be successfully processed by moisture agglomeration by means of the process. Even in the case of sensitive products, no, or only minimal, degradation reactions occur.

Agglomerates in the size range between 200 and 3000 μm, preferably between 200 and 2000 μm, can be produced by the process according to the invention.

The agglomerates produced by the process are extremely highly redispersible. Even for redispersion in cold water, only very short times are required (usually less than 1 minute, preferably <30 seconds), which can be achieved for granules which are produced by customarily employed agglomeration processes (mixer agglomeration, fluidized-bed agglomeration) only with redispersion in hot water.

For bad-tasting products, good taste masking is achieved in the processing with good-tasting products and/or flavourings.

If appropriate process conditions are selected (in particular if a sufficiently high binder content is selected), it is possible not only to agglomerate insoluble products but also partially to enclose them. In this case, the surface of the insoluble particles is coated with the dissolved binder, if the binder solutions are spreadable on the insoluble product. In this case, a surface coverage of 40 to 80%, preferably 50 to 70%, can be achieved. This has the advantage that the products thus enclosed have a reduced reactivity to other mixing constituents. Thus, mixtures of substances can also be produced which usually have only a decreased storage stability.

The very good agglomerate solubility is due to the fact that the bridges between the (insoluble) particles to be agglomerated comprise a very freely soluble material (binder dissolves in fractions of a second in the condensed steam), which is also very well wetted by water. The bridges between the particles are, furthermore, only a few μm thick (1 to 30 μm, preferably 5 to 15 μm) and concentrate at the points of contact between the particles. A high surface area is thus offered for a dissolution process.

Figure 2:
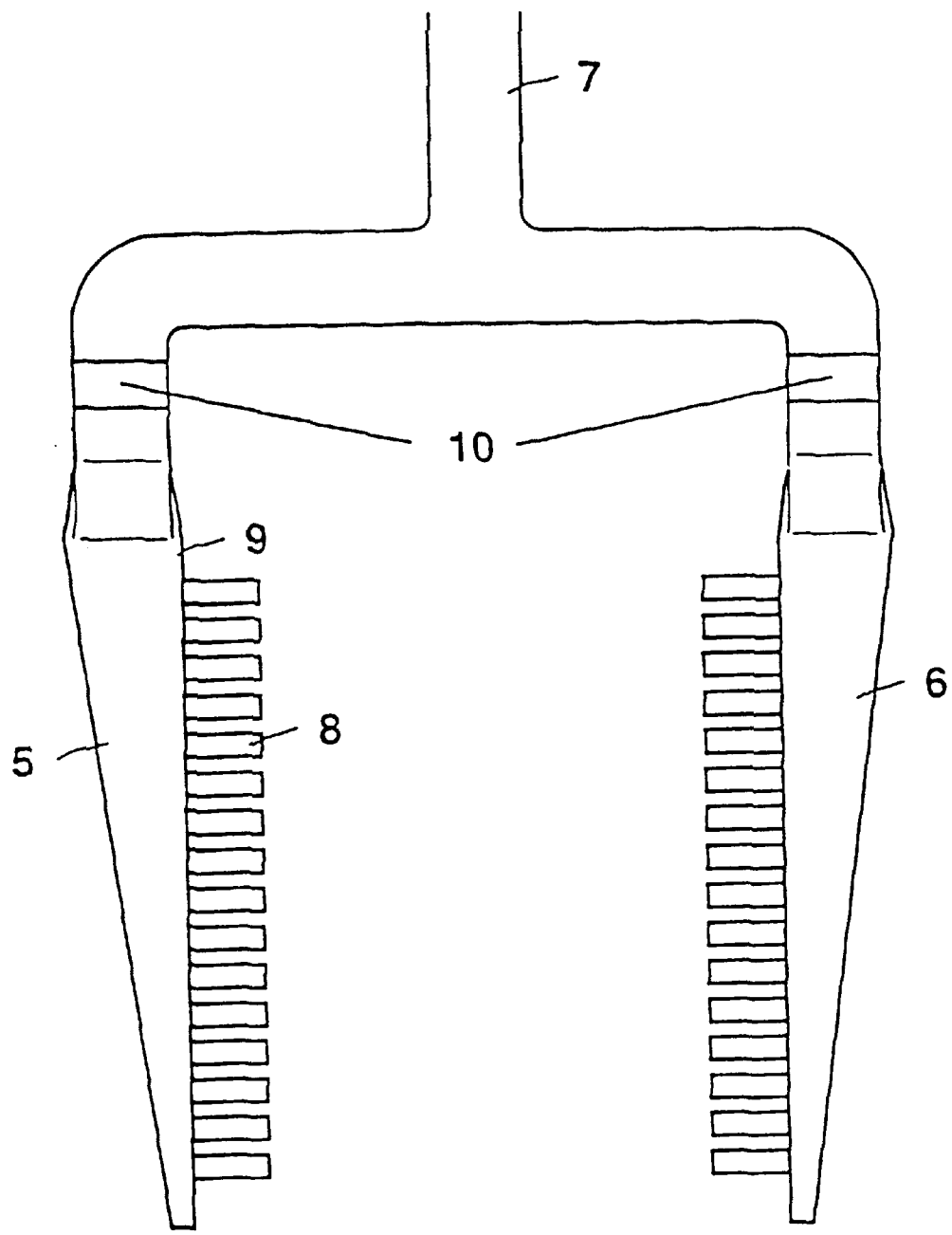
Figure 3:
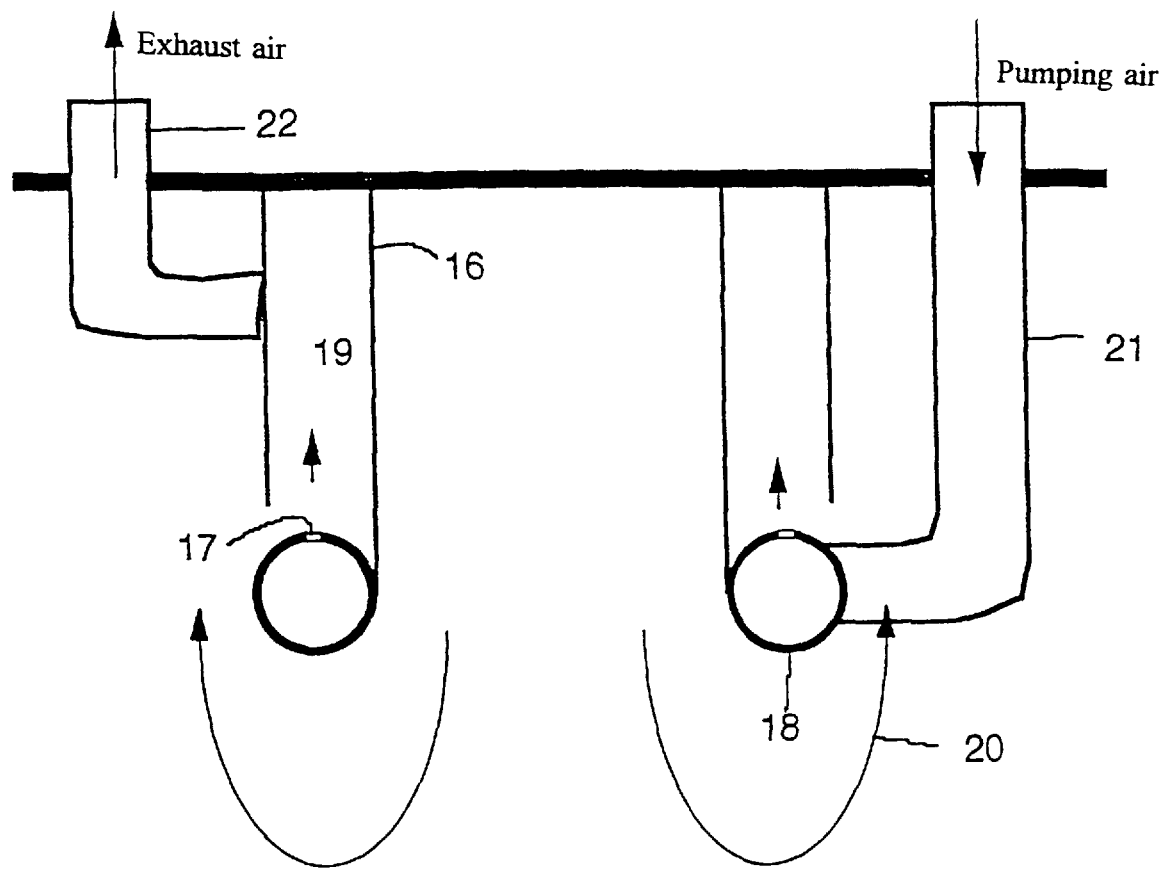
Figure 4:
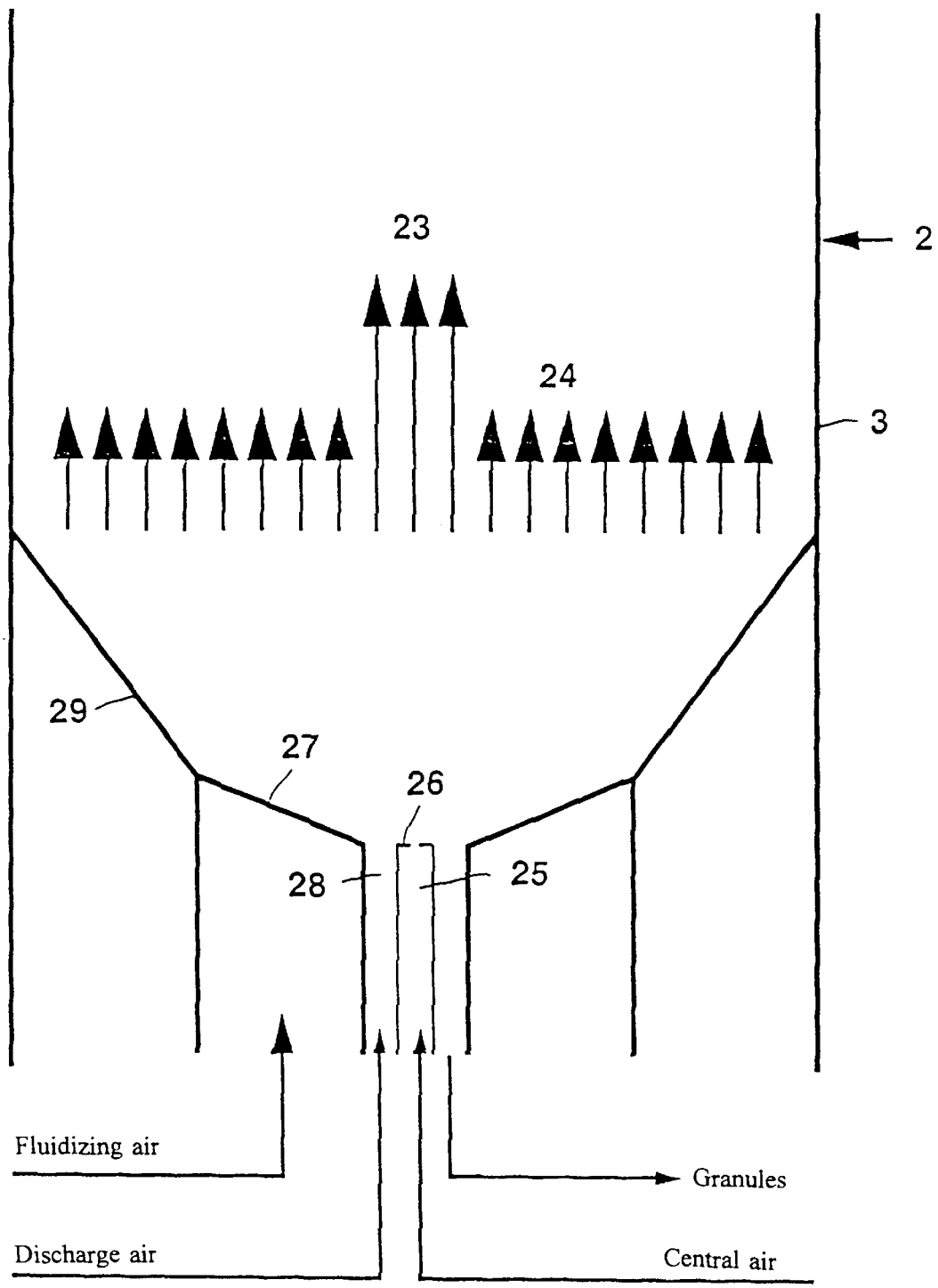

The invention is described in more detail below with reference to working examples and drawings. In the drawings:

FIG. 1 diagrammatically shows the steam jet agglomeration apparatus having an integrated fluidized-bed dryer FIG. 2 shows a plan view of the steam jet nozzles equipped with the distributor tubes FIG. 3 shows the protective tube for the functional separation of moistening and drying of the descending product curtain FIG. 4 shows an enlargement of the integrated fluidized-bed dryer.

According to FIG. 1, the steam jet agglomerator 1 and the fluidized-bed dryer 2 are arranged vertically one above the other and are enclosed by the same housing 3. The agglomerated product 4 leaving the steam jet agglomerator 1 falls directly into the fluidized-bed dryer 2. The steam is fed via two steam jet nozzles 5 and 6 which are connected in parallel and arranged on both sides of the descending product curtain. These are supplied by a shared steam line 7. The steam jet nozzles 5, 6 are, furthermore, pivotable about the angle α. As shown in FIG. 2, the steam jet nozzles 5, 6 each consist of a multiplicity of short tubes 8 or bore holes which are connected to a distributor tube 9 extending in the longitudinal direction of the agglomerator. The cross-section of the distributor tubes 9 decreases over their length in such a manner that the nozzle tubes 8 are impinged by the same steam flow rate. The length of the nozzle tubes 8 is at least three times their diameter. The distributor tubes 9 and thus also the nozzle tubes 8 are pivotable about the point of rotation 10, so that the angle at which the steam impacts the product curtain is adjustable. The product curtain trickling past the steam nozzles 5, 6 is impinged by the steam within a steam action path d, whose length is essentially determined by the exit velocity of the steam and the pivot angle α. This steam action path is termed "steam zone" below. The angle α is adjustable between 0° and 60°. Optimum values are between 20° and 40°.

The solids are fed via a metering screw 11 into a longitudinal hopper 12, at the lower end of which a uniform pulverulent product curtain exits through a slot and passes into the agglomeration section 1. The particles are thus brought into proximity with one another, but no compacting forces occur. The region above the solids feed is likewise covered by a separate cover 13, so that penetration of infiltrated air into the apparatus is avoided, or only a controllable amount of air passes into the apparatus via the product feed. Excessive infiltrated air would lead to a disruption of the steam atmosphere and to impairment of the agglomeration action.

The product to be agglomerated and the binder are fed as a mixture to the metering screw 11. The product in the reservoir can be heated or cooled by means of a heating or cooling medium, e.g. by conditioned air. The product temperature, i.e. the temperature of the powder mixture in the metering screw, is a settable process parameter, which influences the amount of steam which condenses and thus directly influences the agglomeration result (agglomerate size, agglomerate moisture).

An important precondition to achieve reproducible process conditions and thus uniform product qualities is the spatial separation of the steam-treatment zone and drying zone, so that on steam-treatment, a virtually pure steam atmosphere is ensured. For this purpose, a ring gap 14 is provided on the housing 1 at the height of the point at which the steam zone ends and the drying zone begins, which ring gap is connected to a collection line 15. All of the exhaust air originating from the fluidized-bed dryer 2 is taken off through this ring gap. In practice, the ring gap 14 is at a distance of 50 mm to 300 mm below the lower edge of the distributor tubes 9.

An alternative possibility for spatially separating the steam-treatment zone and drying zone is plated on a protective cylinder (see FIG. 3) surrounding the steam zone. The protective cylinder 16 arranged on the cover 13 concentrically to the housing 1 is constructed with double walls. Hot air is injected into this jacket from below through a circular slot 17 in a ring tube 18 in order to heat the protective cylinder 16 and to prevent steam from condensing on its walls. Furthermore, the ring tube 18 is mounted on the protective cylinder 16 in such a manner that a ring gap 19 remains between the jacket and the ring tube 18. Owing to the injector action of the injected hot pumping air, air from the interior is drawn in (arrows 20) through this orifice at the lower rim of the jacket, so that a uniform take-off of the exhaust air from the dryer is ensured over the entire periphery. The hot pumping air is fed to the ring tube 18 through the pumping air branch 21. The exhaust air is taken off from the jacket through the exhaust air branch 22.

In the steam zone, the product curtain is moistened by condensation and as a result the agglomeration is induced. After the moistening, the agglomerated moist product first falls through a countercurrent stream of conditioned drying air originating from the fluidized-bed dryer and is pre-dried as a result. The subsequent drying to the desired final moisture is performed in an integrated fluidized bed. The desired residual moisture is achieved by means of the height of the fluidized bed and by the choice of appropriate drying conditions (air temperature, air flow rate). The contents of the fluidized bed are kept constant at a desired value using a conventional level controller. The final moisture of the product can thus be set exactly, independently of the agglomerate moisture achieved in the steam zone. The desired residual moisture is, in each case, not set until the formation of the solid bridges is completed. The granule size and granule structure depend on the formulation and the selected operating data (ratio of solids rate to steam flow rate, solids temperature, drying conditions). Recirculating solids circuits, which can lead to separations, are not necessary.

According to FIG. 4, the fluidized bed in the dryer 2 is divided into various regions of differing fluidization intensity (flow arrows 23 and 24). In the centre, the bed is fluidized more intensively, by means of a separate central tube 25 having a perforated plate 26, than in the peripheral region in which the fluidization is carried out in a known manner by a conical perforated plate 27 ascending towards the outside. By this means, any still-moist product occurring is immediately mixed with previously dried product and thus prevented from further granulation or clumping (sticking of the previously agglomerated particles to one another). This avoids the moist agglomerates which impact the fluidized bed from further agglomerating, sticking together and leading to the collapse of the fluidized bed. Between the perforated plate 26 and the central tube 25 is arranged an annular discharge gap 28 through which the dried end product is removed in accordance with the contents of the fluidized bed, i.e. in accordance with its mean residence time in the apparatus. This also ensures that no product can leave the apparatus directly, i.e. without prior circulation through the fluidized bed. Directly above the perforated plate 27, the apparatus widens. This likewise conical widening 29 (towards the housing 1) reinforces the uniform circulation movement of the product and thus the distribution of the still-moist impacting agglomerate and promotes the movement of particularly coarse particles towards the discharge 28. By means of the combined measures of the specific varied fluidization and the widening of the apparatus, a particularly uniform product circulation is ensured.

The steam jet agglomeration apparatus according to the invention having an integrated fluidized bed is operated with the following process parameters and product characteristics:

| Flow rates | |
|---|---|
| Steam | 5 to 10 kg/h |
| Solids | 10 to 100 kg/h |
| Residence times | |
| Steam zone | 0.5 to 3 s (prefer-ably 0.5 to 1.5 s) |
| Fluidized bed | 10 to 20 min |
| Temperatures | |
| Steam | 100° C. |
| Fluidizing air | 20 to 80° C. |
| Bed temperature | 20 to 50° C. |
| Product | 0 to 60° C. |
| Product characteristics | |
| Particle size <300 $\mu$m (preferably <200 $\mu$m) | |
| Binder content | 5 to 90 % |
| Agglomerate | |
| Maximum moisture (downstream of the steam zone) | approx. 4 to 5% |
| Final moisture (downstream of the fluidized-bed drying) | <0.5% |
| Agglomerate size | 200 to 2000 $\mu$m |

WORKING EXAMPLES

Example 1

100 g of ASA powder are mixed with 50 g of xylitol as binder. The mixture, which is at room temperature, is introduced by means of the screw 11 into the agglomeration apparatus in such a manner that a long uniform product curtain is formed. The solids mass flow rate is 20 kg/h. It is sprayed with 7 kg/h saturated steam at an angle $\alpha=30°$. The residence time in the steam zone and thus the contact time with the steam is 1 s. This forms granules in the size range preferably between 150 and 1000 $\mu$m. The granules, directly after leaving the steam-treatment zone, have moistures between 1.5% and 3% (determined using the Karl-Fischer titration method). The granules are then dried to residual moistures below 1% in the downstream fluidized bed at bed temperatures of 40° C. The residence time in the fluidized bed is between 10 and 20 min. The ASA/xylitol granules thus produced are readily flowable, have a good taste and are outstandingly redispersible. The content of undesirable degradation products is below 0.5%.

Example 2

100 g of ASA powder are mixed with 200 g of xylitol as binder. The mixture, present at room temperature, is introduced by means of the screw 11 into the agglomeration apparatus in such a manner that a long uniform product curtain is formed. The product mass flow rate is 30 kg/h. It is sprayed with 10 kg/h of steam (saturated) at an angle $\alpha=400$. This forms granules in the size range preferably between 150 and 1000 µm. The granules, directly after leaving the steam-treatment zone, have moistures between 2.5 and 4% (according to Karl-Fischer titration). The granules are dried to residual moistures below 1% in the downstream fluidized bed. The ASA/xylitol granules thus produced are readily flowable, have a good taste and are outstandingly redispersible. The content of undesirable degradation products lies below 0.5%. The surface of the ASA particles is 50 to 70% covered with xylitol. It is thus possible to mix and store the ASA together with other components with which a joint mixture has not been possible hitherto, e.g. with effervescent constituents or other basic components.

Example 3

100 g of ASA powder are mixed with 30 g of sucrose and 5 g of flavouring, preheated to 50° C. and introduced by means of the screw 11 into the agglomeration apparatus in such a manner that a long uniform product curtain is formed. The product mass flow rate is 20 kg/h. It is sprayed with 6 kg/h of steam at an angle $\alpha$ of 30°. Granules in the size range between 200 and 1400 µm are preferentially formed. The granules, directly after leaving the steam-treatment zone, have moistures between 1 and 2.5% (according to Karl-Fischer titration). The granules are dried to residual moistures below 0.5% in the downstream fluidized bed. The granules thus produced are readily flowable, have a good taste and are outstandingly redispersible. The content of undesirable degradation products of ASA is below 0.5%, the loss of customarily volatile aroma substances is below 10%. In this manner, it is possible to agglomerate ASA together with flavourings. This offers the advantage that, in contrast to the conventional procedure, mixing flavourings only for this purpose, separation in the course of further processing, transport and storage up until use is prevented.

Example 4

100 g of ASA are mixed with 50 g of sodium sulphate and agglomerated by steam jet as described in Example 1. After gentle drying, a readily flowable agglomerate which can be very rapidly dispersed in water is obtained with this formulation also, which agglomerate can be employed for sachet or tablet formulations.

Example 5

500 g of paracetamol are mixed together with 100 g of citric acid, 400 g of orange flavouring, 1000 g of lemon flavouring and 2000 g of maltitol as binder. The mixture is introduced at room temperature by means of the screw 11 into the agglomeration apparatus in such a manner that a long uniform product curtain is formed. The solids mass flow rate is 40 kg/h. It is sprayed with 10 kg/h of steam at an angle $\alpha$ of 20°. The residence time in the steam zone and thus the contact time with the steam is 1 s. This preferentially forms granules in the size range between 200 and 2000 µm. The granules, directly after leaving the steam-treatment zone, have moistures between 2 and 4%. The granules are then dried to residual moistures below 0.5% in the downstream fluidized bed at bed temperatures of 30° C. The residence time in the fluidized bed is between 15 and 20 min. The agglomerate thus produced is readily flowable, has a good taste and is outstandingly redispersible. The ratios between the components after the agglomeration correspond to the ratio set in the initial mixture, i.e. no undesirable separation phenomena occur. The agglomerate can serve as a sachet formulation or else as a tablet formulation. The agglomerate dissolves in cold water (5 g in 100 ml) in a time of less than 15 s into a useable beverage.

We claim:

1. Apparatus for agglomerating a slightly-soluble and hydrolytically sensitive substance, comprising an agglomerator (1) having a closed housing (3), at the upper end of which a metering apparatus (11) for a pulverulent material connected to a feed hopper (12) is mounted, by which a freely falling product curtain of the pulverulent material is produced in the agglomerator, and having steam jet nozzles (5,6) in the upper part of the agglomerator for producing steam jets which at least partially surround the freely falling product curtain within a steam zone, wherein at the lower part of the agglomerator (1) a fluidized-bed dryer (2) is connected in such a manner that the agglomerated particles (4) fall directly into the fluidized bed.

2. Apparatus according to claim 1, wherein the steam jet nozzles (5,6) consist of tubes (8) or bore holes which are connected to a distributor tube (9) extending in the longitudinal direction of the agglomerator (1) and wherein one distributor tube (9) is arranged on each of the two sides of the product curtain.

3. Apparatus according to claim 1, wherein a heated double-walled protective tube (16) which encloses the steam jet nozzles (5,6) is arranged in the upper part of the agglomerator (1), through the jacket of which protective tube (16) exhaust air is taken off from the apparatus.

4. Apparatus according to claim 1, wherein a ring gap (14) having a collection line (15) for taking off the exhaust air is provided on the agglomerator housing (3) at a distance of 50 mm to 300 mm from the lower end of the distributor tubes (9).

5. Apparatus according to claim 1, wherein the fluidized-bed dryer (2) has an annular, conically ascending outer fluidizing plate (27) and a central inner fluidizing plate (26) and wherein the flow velocity of the fluidizing air exiting at the inner plate (26) is greater than the flow velocity of the fluidizing air at the outer plate (27).

6. Apparatus according to claim 5, wherein a likewise conical widening (29) toward the agglomerator housing (3) adjoins the conical outer fluidizing plate (27).

* * * * *